United States Patent [19]

Ver der Plank et al.

[11] Patent Number: 5,071,975

[45] Date of Patent: * Dec. 10, 1991

[54] PROCESS FOR PREPARING POLYOL FATTY ACID POLYESTERS

[75] Inventors: Pleun Ver der Plank, De Lier; Adrianus Rozendaal, Vlaardingen, both of Netherlands

[73] Assignee: Van den Bergh Foods Co., Division of Conopco Inc., Lisle, Ill.

[*] Notice: The portion of the term of this patent subsequent to Apr. 9, 2008 has been disclaimed.

[21] Appl. No.: 76,418

[22] Filed: Jul. 21, 1987

[30] Foreign Application Priority Data

Jul. 23, 1986 [NL] Netherlands .................... 8601904

[51] Int. Cl.$^5$ .................. C07B 41/12; C07H 13/06
[52] U.S. Cl. .................. 536/119; 536/115; 536/124; 260/398
[58] Field of Search .................. 536/115, 124, 119; 260/398, 415

[56] References Cited

U.S. PATENT DOCUMENTS

| | | | |
|---|---|---|---|
| 2,893,990 | 7/1959 | Hass et al. | 260/234 |
| 2,948,717 | 8/1960 | Babayan et al. | 536/119 |
| 3,435,024 | 3/1969 | Nobile et al. | 536/4.1 |
| 3,558,597 | 1/1971 | von Vrachel et al. | 260/234 |
| 3,600,186 | 8/1971 | Mattson et al. | 99/1 |
| 3,644,333 | 2/1972 | Osipow et al. | 260/234 |
| 3,792,041 | 2/1974 | Yamagishi et al. | 260/234 |
| 3,963,699 | 6/1976 | Rizzi et al. | 260/234 |
| 3,996,206 | 12/1976 | Parker et al. | 536/119 |
| 4,005,195 | 1/1977 | Jandacek | 514/54 |
| 4,005,196 | 1/1977 | Jandacek et al. | 426/658 |
| 4,032,702 | 6/1977 | James | 536/119 |
| 4,034,083 | 7/1977 | Mattson | 514/54 |
| 4,241,054 | 12/1980 | Volpenhein et al. | 536/115 |
| 4,264,583 | 4/1981 | Jandacek | 536/115 |
| 4,298,730 | 11/1981 | Galleymore et al. | 536/119 |
| 4,334,061 | 6/1982 | Bossier, III | 536/119 |
| 4,368,213 | 1/1983 | Hollenbach et al. | 426/590 |
| 4,377,685 | 3/1983 | Bouniot et al. | 536/119 |
| 4,382,924 | 5/1983 | Berling et al. | 536/119 |
| 4,446,165 | 5/1984 | Roberts | 426/602 |
| 4,496,547 | 1/1985 | Kawashima et al. | 536/115 |
| 4,517,360 | 5/1985 | Volpenhein | 536/119 |
| 4,518,772 | 4/1985 | Volpenhein | 536/119 |
| 4,611,055 | 9/1986 | Yamamoto et al. | 536/115 |
| 4,696,916 | 9/1987 | Yabushita et al. | 514/25 |
| 4,710,567 | 12/1987 | Kea et al. | 536/119 |
| 4,778,881 | 10/1988 | Nieuwenhuis et al. | 536/119 |
| 4,822,875 | 4/1989 | McCoy et al. | 536/119 |

FOREIGN PATENT DOCUMENTS

| | | |
|---|---|---|
| 50-96518 | 7/1975 | Japan . |
| 51-39621 | 4/1976 | Japan . |
| 1332190 | 10/1973 | United Kingdom . |
| 2081266 | 2/1982 | United Kingdom . |

OTHER PUBLICATIONS

"A Solvent Free Synthesis of Sucrose Polyesters", J. Am. Oil Chem. Soc. 55 (1978), 398–401 (G. P. Rizzi and H. M. Taylor).

*Primary Examiner*—Johnnie R. Brown
*Assistant Examiner*—Nancy S. Carson
*Attorney, Agent, or Firm*—Gerard J. McGowan, Jr.

[57] ABSTRACT

A process for preparing polyol fatty acid polyesters, e.g. sucrose polyesters (SPE) is improved by (1) mixing the polyol with an alkaline catalyst such as KOH, NaOH or their carbonates, preferably in aqueous solution or dissolved in $C_{1-5}$ alcohols or ketones at atmospheric pressure and 10°–80° C.

(2) preparing a mixture of fatty acid lower alkyl esters with an emulsifier, preferably a fatty acid soap, and (3) adding the alkaline polyol solution to the mixture of (2), whereby preferably the solvent is removed during the addition of (1) to (2), e.g. at 60° C. and 5 mbar.

The ratio fatty acid lower alkyl esters:polyol is preferably (10–20):1.

The reaction is improved so that SPE are formed at 110°–145° C. within 5–10 hours.

22 Claims, No Drawings

PROCESS FOR PREPARING POLYOL FATTY ACID POLYESTERS

The present invention relates to a process for the preparation of polyol fatty acid polyesters, in which one or more fatty acid lower alkyl esters are reacted with a polyol having at least 4 hydroxyl groups in the presence of an alkaline catalyst, and the polyol fatty acid polyesters formed are separated from the other reaction products and starting materials. In particular, this is concerned, with a new preparation of sucrose polyesters of fatty acids (SPE).

Further, the invention relates to the use of the polyol fatty acid polyesters thus prepared in foodstuffs and pharmaceutical preparations.

In this specification, what is meant by "polyol fatty acid polyesters" are fatty acid polyesters of a polyol having at least 4 hydroxyl groups, of which more than half of the hydroxyl groups have been esterified with fatty acid. For SPE this means at least 5 hydroxyl groups esterified with fatty acid.

These compounds are known to be practically indigestible for human beings. Moreover, on the ground of their physical and organoleptic properties, they are suitable as fat replacers. Because of these properties, the use of polyol fatty acid polyesters is recommended for, inter alia, low-calorie foodstuffs, particularly for people who have great difficulty with slimming. Furthermore, these polyol fatty acid polyesters have certain pharmaceutical effects, because of their being able to take up fat-soluble substances, such as cholesterol, in the gastrointestinal tract and remove them from the body. The use in fat-containing compositions of polyol fatty acid polyesters, in which more than half of the hydroxyl groups have been esterified with fatty acid, is described, inter alia, in U.S. Pat. Nos. 3,600,186 (F. H. Mattson and R. A. Volpenhein), 4,005,195 (R. J. Jandacek), 4,005,196 (R. J. Jandacek and F. H. Mattson), 4,034,083 (F. H. Mattson), 4,241,054 (R. A. Volpenhein and R. J. Jandacek), 4,264,583 (R. J. Jandacek), 4,368,213 (E. J. Hollenbach and N. B. Howard), 4,382,924 (K. G. Berling and T. G. Crosby) and 4,446,165 (B. A. Roberts).

The most important group of polyols having at least 4 hydroxyl groups as described in literature about this subject is that of the sugar polyols, which group comprises the sugars, namely mono-, di- and tri- saccharides, the corresponding sugar alcohols and derivatives thereof having at least 4 hydroxyl groups. In literature many examples of sugar polyols are described, including the sugars lactose, maltose, raffinose and sucrose, the sugar alcohols erythritol, mannitol, sorbitol and xylitol and the sugar derivative alpha-methylglucoside (=alpha-methylether of glucose). The best known polyol fatty acid polyesters are the fatty acid polyesters of sucrose.

The aforementioned process is known. It is described, inter alia, in U.S. Pat. Nos. 3,963,699 (G. P. Rizzi and H. M. Taylor), 4,517,360 (R. A. Volpenhein) and 4,518,772 (R. A. Volpenhein) and J. Am. Oil Chem. Soc. 55 (1978), 398–401 (G. P. Rizzi and H. M. Taylor).

The known processes for the preparation of polyol fatty acid polyesters all have their specific drawbacks.

Thus, the RIZZI/TAYLOR process for the preparation of, inter alia, SPE has to be carried out in two steps, during which actually partial (=lower) sucrose fatty acid esters are first formed, which in the second step are converted into (higher) sucrose fatty acid polyesters so as to obtain a sufficiently high yield. Moreover, the catalysts used, and the way in which they are used, give an increased risk of forming by-products, e.g. via ester condensation, leading to the formation of beta-keto-esters, and e.g. via the reducing effect of NaH, the recommended catalyst in the RIZZI/TAYLOR process.

True, the VOLPENHEIN improvements of the RIZZI/TAYLOR process, in which other catalysts and/or a higher soap: polyol ratio are used, make it possible to carry it out as a one-step process, but in doing so the drawback remains that two of the substances to be reacted, viz. sucrose and the alkaline catalyst, are added as powders, consequently as a heterogeneous system, making it considerably difficult to start the reaction.

For that matter, in the VOLPENHEIN process according to U.S. Pat. No. 4,518,772 the same catalysts can be used as in the RIZZI/TAYLOR process, with the drawbacks associated therewith.

Although in the VOLPENHEIN U.S. Pat. No. 4,517,360 it is stated that using $K_2CO_3$, $BaCO_3$ or $Na_2CO_3$ gives a higher yield than using the catalysts of the RIZZI/TAYLOR process, this appears insufficiently from the comparative tests given in this patent publication: For the carbonates, octa-ester yields of nett 31.6% (=79% ×40% for $Na_2CO_3$) −72.7% (=92% x 79% for $K_2CO_3$) are given and for the RIZZI/TAYLOR catalysts NaH, NaOMe and KH nett yields of 27.4% (=76%×36% for NaH) −64% (=80%×80% for KH), pointing to a large overlapping area and no distinct improvement. Furthermore, all tests were carried out with the higher soap : polyol ratio, which in U.S. Pat. No. 4,518,772 is indicated as an improvement so that it may be wondered whether using the catalysts indicated in U.S. Pat. No. 4,517,360 provides in itself an improvement of the RIZZI/TAYLOR process.

In addition to the above-mentioned publications on the preparation of polyol fatty acid polyesters, many publications are known relating to the preparation of partial polyol fatty acid esters, namely mono-, di- and tri-esters that are suitable as emulsifiers. As an example, British patent specification GB 1,332,190 (Dai Ichi) is mentioned, in which the preparation of partial sucrose fatty acid esters is described. Thus, sucrose, fatty acid soap and water are mixed such that the sucrose is completely dissolved. To this solution a methyl ester of a fatty acid having 8–22 carbon atoms and a transesterification catalyst are added and the mixture is gradually heated under a gradually decreasing pressure until a substantially completely dehydrated melt is obtained without any substantial loss of fatty acid ester through hydrolysis, after which the resulting melt is kept at a temperature of 110°–175° C. to permit transesterification of the fatty acid methyl ester by the sucrose. Hydroxides, carbonates, bicarbonates, methoxides, ethoxides, and propoxides of potassium, sodium and lithium can be used as the transesterification catalyst.

According to this publication, the presence of soap in the aqueous sucrose solution is required to avoid aggregation of the powdery sucrose. The catalyst has to be added after the mixture of soap and sucrose has been prepared.

A serious disadvantage of this method is foam formation, which can occur during removal of the water, resulting in practical problems during application of this process on a technical scale.

Consequently there is still need of a relatively simple process for the preparation of polyol fatty acid polyesters with as little formation of by-products and troublesome foam formation as possible.

It has now been found that polyol fatty acid polyesters, in particular of sucrose, can be prepared in an elegant way if sucrose is first dissolved in aqueous KOH, separately a mixture of methyl esters and soaps is made, after which the alkaline sucrose solution is added to the mixture of soap/methyl ester under vacuum, during which at least part of the water is removed practically instantaneously. If desired, the soaps corresponding to the methyl esters used can be applied. The use of potassium soaps is preferred. After the mixture formed has been dried under vacuum, the mixture is heated to about 110°-140° C. to start SPE formation, which can be seen from the formation of methanol. When the reaction is completed, the formation of methanol will stop.

Based on this finding and further experiments, the invention now provides a process for the preparation of polyol fatty acid polyesters, in which one or more fatty acid lower alkyl esters are reacted with a polyol having at least 4 hydroxyl groups in the presence of an alkaline catalyst and the polyol fatty acid polyesters formed are separated from the other reaction products and starting materials, which is characterized in that (1) the polyol is mixed with the alkaline catalyst, forming a liquid system, if required using a non-toxic or easily removable solvent, in which system the alkaline catalyst may react with the polyol forming a catalytically active polyol anion, and (2) this liquid system, optionally after any solvent used has first been removed, is combined with excess fatty acid lower alkyl esters preferably containing a emulsifier, and the mixture thus formed is reacted under conditions such that the polyol fatty acid polyesters are formed.

In this specification polyol also comprises a partial fatty acid ester of a polyol, which partial esters are intermediates in the conversion of polyol into polyol fatty acid polyesters.

Preferably a sugar polyol is used and particularly sucrose.

Suitable alkaline catalysts include the group consisting of alkali metals and alkaline earth metals, and the alkoxides, bicarbonates, carbonates, hydrides, hydroxides and alloys of these metals. KOH has been found to be particularly suitable as a cheap and effective alkaline catalyst, but also NaOH and the carbonates or bicarbonates of K or Na can be used with advantage. Although it can be argued whether the aforementioned KOH acts as a catalyst or as a reagent, which forms the actual catalyst or catalysts in the process, this description uses the term "catalyst", as does known literature about related reactions.

It is recommendable that in step (1) a solvent be used to improve the contact and, as a result, the reaction between polyol and alkaline catalyst. Suitable solvents include lower alcohols and/or ketones, e.g. a $C_{1-5}$-alcohol or -ketone. For sucrose as polyol and KOH as alkaline catalyst, water is a very suitable solvent.

Step (1) was carried out successfully at atmospheric pressure and room temperature. Partly owing to the solubility of sugar, other temperatures can be used as well, e.g. from 10°-80° C. or even from 40°-70° C. Step (1) can also be carried out at a pressure higher or lower than atmospheric.

For practical purposes the alkaline catalyst of step (1) can be added in a molar ratio of catalyst:polyol of about (0.05-1):1.

In principle many types of alkali-resistant emulsifiers can be used to improve contact of the ingredients in the reaction to be carried out in step (2). Known edible emulsifiers include mono/diglycerides, phosphatides, such as lecithin, and detergents such as soaps, sodium dodecyl sulphate and partial sugar esters of fatty acids.

In a particular embodiment of a process according to the invention, a fatty acid soap is incorporated as emulsifier in the fatty acid lower alkyl esters before the addition of the mixture containing the polyol and alkaline catalyst. The required soap can be made beforehand and be added in dry form. However, it is also quite possible that the fatty acid soap is formed in situ by partial saponification of the fatty acid lower alkyl esters or by neutralization of fatty acids added. In that case it is preferable to use a solvent in which an alkaline substance used for the saponification or neutralization can dissolve to improve the contact and, as a result, the saponification or neutralization. Suitable solvents include lower alcohols, preferably a $C_{1-5}$ alcohol, in particular methanol, and/or water. Other alkali-resistant solvents can also be used. When a solvent is used, it is recommendable that after the in situ soap formation the solvent be removed, e.g. by evaporation, before the resulting mixture containing fatty acid lower alkyl esters and soap is processed further in step (2). The amount of soap is preferably about 2-12 wt. % of the total reaction mixture.

Esters of lower alcohols, preferably of $C_{1-5}$ alcohols, are suitable for use as fatty acid lower alkyl esters. The fatty acids can be $C_{8-22}$ fatty acids, both saturated and unsaturated fatty acids. In the preparation of polyol fatty acid polyesters of $C_{8-12}$ fatty acids, starting from lower alkyl esters of $C_{8-12}$ fatty acids, there is a risk of part of the starting fatty acid lower alkyl esters evaporating; in that case, additional measures are to be taken to collect these starting materials and take them back into the reaction mixture.

For preparing sucrose octaesters the theoretical molar ratio of fatty acid lower alkyl esters:sucrose is 8:1. In practice, good results were obtained with molar ratios of 10:1-20:1.

The actual formation of polyol fatty acid polyesters takes place in step (2), which can be carried out at a temperature of about 100°-180° C., preferably 110°-145° C. and at reduced pressure, in particular at about 1-50 mbar.

Although the scope of the invention is not restricted by theoretical statements, on the ground of data known from literature the following reactions can be indicated to illustrate the process according to the invention. It is assumed that in step (1), when sucrose and aqueous KOH are used, a sucrate anion is formed according to the equation

$$(sucr.)OH + OH^- = = = (sucr.)O^- + H_2O,$$

in which "= = =" means "in equilibrium with".

The relevant equilibrium is established almost instantaneously under the conditions used and is largely at the right side. In this connection it could be said that sucrose behaves like a weak acid (cf. J. A. Rendleman, Jr.; Adv. in Carbohydr. Chem. 21 (1966), 209, 239-240, 244 and 246). For all that, when e.g. methyl esters are used, the water present in step (2) should be removed quickly, since the OH-ions still present may cause saponification of methyl esters with the aforesaid equilibrium shifting to the left at the expense of sucrate anion. On prolonged contact of sucrate anion with methyl esters in the presence of water, complete saponification takes place and no sucrate anion is left. When, after removal of the water, the temperature is raised to 110°-145° C., this sucrate anion reacts with a methyl ester molecule according to generally accepted, recent theories on interesterification [cf. J. A. Heldal & P. C. Mork in (Proc.) 11th Scand. Symp. Lipids (1981), 147–152 (Publ. 1982)], in which a fatty acid chain is bound to sugar by means of an ester bond, releasing methoxide anion ($CH_3O^-$). This reacts immediately or simultaneously with a sugar molecule (partially or not partially acylated), with methanol being ultimately formed as visible reaction product.

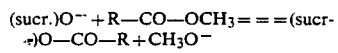

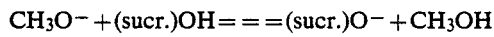

This process is continued until all hydroxyl groups of sucrose have been acylated (or all methyl esters have been used). Then, no methanol is produced any more and isolation of SPE can be proceeded to.

Separation of the polyol fatty acid polyesters from the other reaction products and starting materials can be brought about by processes known per se, inter alia by using organic solvents, water and/or salting out, e.g. according to the process described in the BOSSIER patent U.S. Pat. No. 4,334,061.

In order to establish the degree of conversion, the amount of methanol released was determined.

Taking sucrose and methyl esters as starting products, after removal of the soap left after the reaction, the reaction product will consist of a mixture of methyl esters and sucrose esters of fatty acids. In a number of cases the hydroxyl number of this reaction product that had been freed of soap was determined, which is also a measure for the degree of conversion, whereby, of course, a correction needs to be made for the content of methyl esters in the reaction product. For example, the theoretical values of the hydroxyl number for SPE of groundnut oil fatty acids depends on the degree of conversion as follows:

| SPE (average number of esterified hydroxyl groups) | Hydroxyl number | Degree of conversion in % |
|---|---|---|
| 8 | 0. | 100.0 |
| 7 | 26 | 87.5 |
| 6 | 58 | 75.0 |
| 5 | 101 | 62.5 |
| 4 | 160 | 50.0 |
| 3 | 247 | 37.5 |
| 2 | 386 | 25.0 |
| 1 | 647 | 12.5 |
| 0 | 1310 | 0.0 |

In the tests carried out according to the invention, it appeared that in most cases the hydroxyl number found was less than 10, which corresponds with an average number of esterified hydroxyl groups in the SPE of about 7.6 or more, amounting to a degree of conversion of about 95% or more.

Another indication of the conversion can be obtained by means of a mass balance for the sucrose esters. In most cases this balance was in agreement with the conversion of methanol and/or the hydroxyl number found.

The process according to the invention further has, inter alia, the advantage that less foam is formed in the various steps of the process. It has been found that, especially when aqueous KOH is used instead of KOH/methanol, less foam occurs when soap is formed in situ. Likewise, when the Water is removed quickly under vacuum, less foam is formed than when KOH/methanol is used.

Furthermore, it appears in practice that, when the RIZZI/TAYLOR process is carried out on a pilot plant scale with catalysts like NaH or sodium methoxide, formation of foam can also occur at a degree of conversion of about 60–70%, accompanied by the formation of poor products which caramellize during steaming at 190° C. in the ultimate refining. The foaming problems mentioned do not arise, or to a far lesser degree, when using the process according to the invention, in particular when in step (2) aqueous KOH is used for forming soap in situ from the methyl esters or from the fatty acids and in step (1) for the formation of the liquid system containing polyol and alkaline catalyst.

The invention further relates to the polyol fatty acid polyesters prepared by a process according to the invention.

The invention also relates to a process for the preparation of foodstuffs, in which a substantial amount of polyol fatty acid polyester is incorporated which has been prepared according to the invention. Preference is expressed for the preparation of a low-calorie foodstuff, in which a non-digestible polyol fatty acid polyester is incorporated as essential fat component.

Another aspect of the invention is a process for the preparation of pharmaceutical preparations, there being incorporated in such a preparation a polyol fatty acid polyester which has been prepared according to the invention.

The invention is now illustrated by the following Examples without, however, being restricted thereto.

In Examples I–VIII an emulsifier soap was used which was prepared in situ. In Examples I and VIII this was done by partial saponification, in Examples II–VII by neutralization of fatty acids added.

EXAMPLE I

Step 1. Forming of the liquid system containing the sucrose and alkaline catalyst 25.4 9 (74.3 mmol) sucrose and 0.896 g 85% KOH (13.6 mmol) were dissolved in 25 ml water at room temperature and at atmospheric pressure.

Step 2a. Forming of soap 8 g 85% KOH (0.12 mol) dissolved in 60 ml methanol was added to 125 g methyl ester of groundnut oil fatty acids (0.422 mol). The methanol was removed by boiling, followed by drying at 100°–110° C. and 1-2 mbar. Subsequently 225 g (0.760 mol) methyl ester of groundnut oil fatty acids was added.

Step 2b. Reaction

With vigorous stirring at 60° C. and 2 mbar, the sucrose-containing alkaline solution of step (1) was added to the reaction product of step (2a), resulting in quick removal of the water during the addition. Thereafter, drying was carried out under the same conditions for about 30 minutes, resulting in a water content of less than 0.04%. Subsequently the temperature was raised to 120° C., after which sugar ester started to form. This could be observed by development of methanol, which was collected in a cold trap.

The molar ratio KOH:sucrose in step (1) was 0.183 and that of methyl ester:sucrose was 14.3. The amount of soap was 10.2%, calculated on the total reaction mixture.

The yield of methanol collected after reaction for 10 hours was 88% of the maximum amount of octa-ester calculated theoretically.

EXAMPLE II

As in Example I, sucrose (25.4 g=74.3 mmol) and 85% KOH (1.054 g=16 mmol) were dissolved in water (25 ml).

Subsequently a mixture of methyl esters of groundnut oil fatty acids (314 g=1061 mmol) and fatty acids cc (32.67 g=121 mmol of the product Pristerene 4911 ®, ex Unichema, mainly consisting of saturated $C_{16-18}$ fatty acids) was prepared, to Which a solution of 85% KOH (8 g=121 mmol) in water (10 ml) was added at 60° C. under vacuum.

Thereafter, the sucrose/sucrate solution was added to the soap dispersion in about 30 minutes at 60° C. and 2 mbar. Further drying was then carried out for 30 minutes at 60° C. and 2 mbar and the mixture was subsequently heated to 125° C., after which methanol started to develop. After reaction for 10 hours under these conditions, when 95% of the theoretical amount of methanol had been collected, calculated on complete conversion of the sucrose into octa-ester, the reaction was stopped by cooling to about 60° C.

After further processing the reaction mixture according to the BOSSIER method with 2-propanol/water in order to remove the soap, a hydroxyl number of 9.8 was measured.

The molar ratio KOH:sucrose in step (1) was 0.215 and the molar ratio methyl ester:sucrose was 14.3. The weight percentage of soap in the total mixture was 0.2.

EXAMPLE III

Example II was repeated, except that the product Pristerene 4941 ®, ex Unichema (36.8 g=121 mmol, mainly consisting of saturated $C_{18-22}$ fatty acids) was now used as fatty acid source. The reaction was carried out at 140° C. instead of 125° C. After 6 hours, 99% of the theoretical amount of methanol had been collected. The weight percentage of soap, calculated on the total mixture, was 10.9. The hydroxyl number before steaming but after washing with a mixture of 2-propanol/water for removal of the soap and after drying was 4.

EXAMPLE IV

Example II was repeated, except that the product Prifrac 7960 ®, ex Unichema (containing about 60% linoleic acid and about 22% oleic acid) was used as fatty acid source. After reaction for 9 hours, 95% of the theoretical amount of methanol had been collected.

EXAMPLE V

Example II was repeated, except that methyl esters of fatty acids of soybean oil were used, hardened to 69° C. (314 g=1061 mmol) and, as fatty acid source, the product Priolene 6930 ®, ex Unichema (mainly consisting of oleic acid; 33 g=121 mmol). 10 wt. % soap was used, calculated on the total mixture. After reaction for 9 hours, 96% of the theoretical amount of methanol had been collected.

EXAMPLE VI

Example v was repeated, except that methyl esters of coconut oil fatty acids (244 g=106 mmol) were used and the reaction was carried out at 110°-118° C. 12.5% soap was used, calculated on the total mixture. After 10.5 hours, no methanol was formed any more, after which the reaction mixture was cooled and further processed.

EXAMPLE VII

As in Example I, sucrose (254 g=0.743 mol) and 85% KOH (10.54 g=0.16 mol) were dissolved in 250 ml water.

Subsequently a solution of 85% KOH (80 g=1.21 mol) in 100 ml water was added to methyl esters of soybean oil fatty acids (3500 g=11.82 mol) at 70° C. under 1 atm. nitrogen. After heating for 1.5 hours at 95° C., water and methanol were removed under vacuum. The sucrose/sucrate solution was then added to the soap dispersion at 60° C. and 2 mbar. After drying under the same conditions, the mixture was heated to 125° C. in order to start the reaction; 12 hours later, 99% of the theoretical amount of methanol had been collected.

EXAMPLE VIII

A sucrose/sucrate solution was prepared as indicated in Example II.

Subsequently 22.0 g of the product Pristerene 4941 ®, ex Unichema (=72 mmol) was added to methyl esters of groundnut oil fatty acids (314 g=1061 mmol) at room temperature, which mixture was then neutralized by the addition of 85% KOH solution (4.94 g=75 mmol in 6 ml water) at 60° C. under vacuum. Thereafter, the sucrose/sucrate solution Was added to the soap dispersion as in Example II. After drying for 30 minutes under the same conditions, the mixture was heated to 125° C. in order to start the reaction; about 5 hours later, 100% of the theoretical amount of methanol had already been collected.

The molar ratio KOH:sucrose in step (1) and methyl ester:sucrose was the same as in Example II. The amount of soap was 6.8 wt. %, calculated on the total mixture.

We claim:

1. A process for the preparation of polyol fatty acid polyesters more than half of the polyol hydroxyl groups whereof have been esterified with fatty acids, by reacting one or more fatty acid alkyl esters with a polyol having at least 4 hydroxyl groups in the presence of an alkaline catalyst, comprising the steps of a) mixing the polyol with the alkaline catalyst in the presence of a non-toxic and easily removable solvent selected from the group consisting of $C_{1-5}$ alcohols, $C_{1-5}$ ketones and water, at 10° C. to 80° C. to form a liquid system in which the alkaline catalyst may react with the polyol forming a catalytically active polyol anion, b) combining this liquid system with excess fatty acid lower alkyl ester, c) after removal of the solvent, reacting the mixture thus formed under conditions such that said polyol fatty acid polyesters are formed, and d) separating the polyol fatty acid polyesters so formed, from the other reaction products and starting materials.

2. Process according to claim 1, wherein a sugar polyol is used as polyol.

3. Process according to claim 2 wherein the sugar polyol is sucrose.

4. Process according to claim 1, wherein the alkaline catalyst is selected from the group consisting of alkali metals and alkaline earth metals, and the alkoxides, carbonates, bicarbonates, hydrides, hydroxides and alloys of these metals.

5. Process according to claim 4, wherein KOH is used as alkaline catalyst.

6. Process according to claim 1, wherein step (a) is carried out at atmospheric pressure.

7. Process according to claim 1, wherein in step (a) the alkaline catalyst is added in an amount such that the molar ratio of catalyst to polyol is in the range of about (0.05–1):1.

8. Process according to claim 1, wherein step (b) is carried out at a temperature of about 100°–180° C.

9. Process according to claim 8, wherein step (b) is carried out at a temperature of about 110° to 145° C.

10. Process according to claim 8, wherein step (b) is carried out at a reduced pressure.

11. Process according to claim 10, wherein the reduced pressure is about 1–50 mbar.

12. Process according to claim 2 wherein in step 6 the excess fatty acid lower alkyl esters contain an emulsifier.

13. Process according to claim 12, wherein the emulsifier is a fatty acid soap.

14. Process according to claim 13, wherein the soap is used in an amount of about 2–12 wt. % of the total reaction mixture.

15. Process according to claim 13, wherein the fatty acid soap is formed in situ.

16. Process according to claim 15, wherein the fatty acid soap is formed by partial saponification of the fatty acid esters.

17. Process according to claim 15, wherein the fatty acid soap is formed by neutralization of fatty acids added.

18. Process according to claim 15, wherein om step (a) a solvent is used in which an alkaline substance used for the in situ formation of soap can dissolve.

19. Process according to claim 18, wherein the solvent is selected from the group consisting of $C_{1-5}$ alcohols and water.

20. Process according to claim 18, wherein after the in situ soap formation, the solvent used is removed by evaporation.

21. Process according to claim 1, wherein the fatty acid lower alkyl esters are selected from the group consisting of esters of $C_{8-22}$ fatty acids and $C_{1-5}$ alcohols.

22. Process according to claim 1 wherein the solvent is water.

* * * * *